United States Patent [19]

Glaeser et al.

[11] Patent Number: 4,783,545

[45] Date of Patent: Nov. 8, 1988

[54] METHOD FOR AMMOXIDATION OF PARAFFINS AND CATALYST SYSTEM THEREFOR

[75] Inventors: Linda C. Glaeser, Cleveland Heights; James F. Brazdil, Jr., Mayfield Village; Mark A. Toft, Lakewood, all of Ohio

[73] Assignee: The Standard Oil Company, Cleveland, Ohio

[21] Appl. No.: 137,316

[22] Filed: Dec. 23, 1987

Related U.S. Application Data

[60] Division of Ser. No. 50,268, May 15, 1987, which is a continuation-in-part of Ser. No. 887,478, Jul. 21, 1986, which is a continuation-in-part of Ser. No. 811,842, Dec. 20, 1985, abandoned.

[51] Int. Cl.$^4$ .................................. C07C 120/14
[52] U.S. Cl. ................. 558/319; 502/202; 502/204; 502/205; 502/206; 502/209; 502/215; 502/241; 502/243; 502/244; 502/247; 502/248; 502/249; 502/304; 502/305; 502/306; 502/307; 502/353
[58] Field of Search ................................ 558/319

[56] References Cited

U.S. PATENT DOCUMENTS

| | | | |
|---|---|---|---|
| 3,668,147 | 6/1972 | Yoshino et al. | 502/207 |
| 3,833,638 | 9/1974 | Knox et al. | 558/319 |
| 3,860,534 | 1/1975 | Harris | 502/353 |
| 3,879,453 | 4/1975 | Ono et al. | 260/533 N |
| 4,001,317 | 1/1977 | Grasselli et al. | 502/304 |
| 4,052,418 | 10/1977 | Suresh et al. | 502/210 X |
| 4,065,468 | 12/1977 | Grasselli et al. | 502/211 |
| 4,138,366 | 2/1979 | Shaw et al. | 252/404 |
| 4,148,757 | 4/1979 | Brazdil et al. | 502/206 |
| 4,167,494 | 9/1979 | Grasselli et al. | 252/432 |
| 4,209,640 | 6/1980 | Yamamoto et al. | 562/532 |
| 4,212,766 | 7/1980 | Brazdil et al. | 502/210 |
| 4,217,309 | 8/1980 | Umemura et al. | 568/477 |
| 4,224,187 | 9/1980 | Vanderspurt | 502/304 |
| 4,250,339 | 2/1981 | Sakamoto et al. | 568/471 |
| 4,259,211 | 3/1981 | Krabetz et al. | 252/443 |
| 4,290,920 | 9/1981 | Suresh et al. | 252/439 |
| 4,293,443 | 10/1981 | Suresh et al. | 502/307 |
| 4,307,247 | 12/1981 | Shaw et al. | 562/599 |
| 4,335,018 | 6/1982 | Franz et al. | 252/435 |
| 4,397,771 | 8/1983 | Grasselli et al. | 502/306 |
| 4,414,133 | 11/1983 | Otake et al. | 502/179 |
| 4,415,482 | 11/1983 | Ebner | 502/205 |
| 4,424,141 | 1/1984 | Grasselli et al. | 502/205 |
| 4,436,671 | 3/1984 | Furuoya et al. | 558/375 |
| 4,511,671 | 4/1985 | Saito et al. | 502/242 |
| 4,530,916 | 7/1985 | Matsumoto et al. | 502/209 |

FOREIGN PATENT DOCUMENTS

| | | | |
|---|---|---|---|
| 1336135 | 11/1973 | United Kingdom | 558/324 |
| 1336136 | 11/1973 | United Kingdom | 558/324 |

Primary Examiner—Joseph Paul Brust
Attorney, Agent, or Firm—C. S. Lynch; D. J. Untener; L. W. Evans

[57] ABSTRACT

Ammoxidation of $C_3$ to $C_5$ acyclic alkanes with $NH_3$ and $O_2$ using (1) a mole ratio of alkane:$NH_3$ in the range from 2 to 16 and a mole ratio of alkane:$O_2$ in the range 1 to 10 and (2) a mixture of particulate catalyst compositions, the first being especially effective to promote formation of an unsaturated nitrile and an olefin from the paraffin, and the second catalyst composition being especially effective to promote the conversion of the olefin to the unsaturated nitrile. Catalytic compositions useful in the process are disclosed.

13 Claims, No Drawings

METHOD FOR AMMOXIDATION OF PARAFFINS AND CATALYST SYSTEM THEREFOR

This is a division of co-pending application Ser. No. 050,268, filed May 15, 1987, which is a continuation-in-part of Ser. No. 887,478 filed July 21, 1986, which is a continuation-in-part of Ser. No. 811,842 filed Dec. 20, 1985, now abandoned.

This invention relates to an improved process for the catalytic ammoxidation of paraffins containing from 3 to 5 carbon atoms to $\alpha,\beta$-unsaturated nitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

It is a further object of the invention to provide new catalyst systems for such process.

Still another object is to provide an improved catalytic ammoxidation process for making unsaturated nitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention. There are two main features of the present process invention. The first of these is the use of an excess of the alkane feed with relation to $NH_3$ and molecular oxygen. The second feature, which is used in combination with the high ratio of the $C_3$ to $C_5$ paraffin to $NH_3$ and $O_2$, is that a combination, i.e., a mixture, of catalysts is employed, the first catalyst composition being especially effective to promote formation of an unsaturated nitrile and an olefin from the paraffin, and the second catalyst composition being especially effective to promote the conversion of the olefin to the unsaturated nitrile. Such mixture is the subject of the composition claims herein.

In the present application "paraffin" designates an acylic paraffin. "Rare earths" mean elements 57 through 71.

British Patent Specification Nos. 1,336,135 and 1,336,136 disclose the use of high ratios of propane or isobutane to ammonia and oxygen, but only single ammoxidation catalysts are used, and the yields of acrylonitrile are extremely poor. U.S. Pat. No. 3,860,534 also discloses use of such high ratios, using a catalyst containing only V and Sb oxides. However, after the catalyst is calcined, it is washed for 24 hours with water and dried, a laborious procedure. U.S. Pat. No. 3,833,638 discloses ammoxidation of propane or isobutane with a (Bi,Te) CeMo oxide catalyst of a defined composition, and the disclosed reactant ratios include an excess of paraffin over $NH_3$ and $O_2$, but results are for runs without excess paraffin, and the one-pass yields are low. A. N. Shatalova et al. in Neftekhiniya 8, No. 4, 609-612 (1968), describe the reaction of propane with oxygen and ammonia using a large excess of propane and a mixture of two catalysts, one of which is described as oxides of metals having dehydrogenating characteristics at 550° and 600° C. At 500° C. little or no acrylonitrile was produced. Rather large amounts of propionitrile and acrolein were made per mole of acrylonitrile produced. The per pass conversion of propane to acrylonitrile was generally 2-4 percent with selectivity to acrylonitrile being from 12 to 33 percent.

In the present process when applied to propane ammoxidation a small amount of propylene is produced in relation to the unreacted propane in the effluent. Thus the propane effluent containing propylene in the amount of up to 8 mole percent, but usually no more than 6 mole percent, of the amount of propanee plus propylene can comprise the substrate feed to the present process. And in general the $C_3$ to $C_5$ alkane feed to the process can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. Although larger amounts of $C_3$ to $C_5$ olefins may be present in the substrate paraffin feed, usual amounts are as stated, and the usual olefin is that corresponding to the particular paraffin fed to the reaction zone of the present process.

According to the present invention there is provided a process for the ammoxidation of a $C_3$ to $C_5$ paraffin which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 (usually 3–7), and a mole ratio of paraffin to $O_2$ in the range from 1 to 10 (usually 1.5–5), said first catalyst composition being 10–99 weight percent of a diluent/support and 90–1 weight percent of a catalyst having the components in the proportions indicated by the empirical formula:

formula (1)

where
A is one or more of W, Sn, Mo, B, P and Ge;
G is one or more of Fe, Co, Ni, Cr, Pb, Mn, Zn, Se, Te, Ga, In and As;
J is one or more of an alkali metal and Tl;
T is one or more of Ca, Sr and Ba; and
where m is from 0.01 and up to 20; a is 0.2–10; b is 0–20; c is 0–20 (usually 0–1); t is 0–20; the ratio $(a+b+c+t):(1+m)$ is 0.01–6; wherein x is determined by the oxidation state of the other elements, and wherein the antimony has an average valency higher than +3 and the vanadium has an average valency lower than +5, said second catalyst composition being 0–99 weight percent of a diluent/support and 100–1 weight percent of a catalyst having the components in the proportions indicated by the empirical formula:

formula (2)

where

D is one or more of Fe, Mn, Pb, Co, Ni, Cu, Sn, P, Cr, Y, Mg, Ca, Sr, Ba and rare earths other than Ce and Sm;

E is one or more of Sb, Ge, As, Se, Te and V;

L is one or more of an alkali metal, Tl, Ag and Sm and where n is 0.01-24, p is 0.01-24; (n+p) is 0.1-24, d is 0-10, e is 0-10, f is 0-6, and g is 0-8, and y is determined by the oxidation state of the other elements, wherein the weight ratio in said mixture of said first catalyst composition to said second catalyst composition is in the range of 0.001 to 2.5.

In an especially useful catalyst of formula (1), m is greater than 1 (often 2-10, more often 3-7).

By "particulate mixture" as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

In the present process in all its embodiments the ratio of $O_2$ to $NH_3$ fed to the reaction zone is usually in the range from 1 to 10 (more often 1-5) and the ratio of inert gaseous diluent to paraffin is usually in the range zero to 5 (more often zero to 3).

According to one embodiment of the present invention there is provided a process for the ammoxidation of $C_3$ to $C_5$ paraffin which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing the components alkane/$NH_3$/$O_2$/inert diluent in the mole ratios 8/0.5-1.5/0.1-5/0-5, more usually in the mole ratios 8/0.5-1/0.5-3.5/0-1, said first catalyst composition being 10-99 weight percent of a diluent/support and a 90-1 weight percent of a catalyst having the components in the proportions indicated by the empirical formula:

$$VSb_mA_aG_bJ_cO_x, \qquad \text{formula (3)}$$

where

A is one or mor of W, Sn, Mo, B, P and Ge;

G is one or more of Fe, Co, Ni, Cr, Pb, Mn, Zn, Se, Te, Ga, In and As;

J is one or more of an alkali metal, Ca, Sr, Ba and Tl and where m is greater than 1 and up to 20 (usualy 2-10, most usually 3-7); a is 0-10; b is 0-20; c is 0-20; a is equal to or less than m; b is equal to or less than m; c is equal to or less than m; wherein x is determined by the oxidation state of the other elements, and wherein the antimony has an average valency higher than +3 and the vanadium has an average valency lower than +5, said second catalyst composition being 0-99 weight percent of a diluent/support and 100-1 weight percent of a catalyst having the components in the proportions indicated by the empirical formula:

$$Bi_nCe_pD_dE_eL_fMo_{12}W_gO_y \qquad \text{formula (2)}$$

where

D is one or more of Fe, Mn, Pb, Co, Ni, Cu, Sn, P, Mg, Ca, Sr and Ba;

E is one or more of Sb, Ge, As, Se, Te and V;

L is one or more of an alkali metal, Tl, Ag and Sm and where n is 0.01-24, p is 0.01-24; (n+p) is 0.1-24, d is 0-10, e is 0-10, f is 0-6, g is 0-8, and y is determined by the oxidation state of the other elements, wherein the weight ratio is said mixture of said first catalyst composition to said second catalyst composition is in the range of 0.001 to 2.5.

The diluent or support for either catalyst composition is a refractory metal oxide or mixture, such as silica, silica-alumina, etc.

In the usual practice of the present invention the catalyst support/diluent for the catalyst of formula (1) or (3) is not an oxide of an element named in formula (1) or (3). Further, in the usual practice of the invention the catalyst support/diluent for the catalyst of formula (2) is not an oxide of an element named in formula (2).

In the catalyst compositions of the invention the empirical formulas (1), (2) and (3) do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such element may at times be present as a complex oxide with one, more than one, or all of the elements in formula (1) or formula (2) or formula (3), which complex oxides form during the precipitation or agglomeration, drying and calcining process for preparing the catalyst composition.

The process of the invention is especially useful in the ammoxidation of propane or isobutane.

According to the present invention the foregoing first catalyst composition is prepared under conditions such that in the final composition the average oxidation state of vanadium is less than 5.

One method for preparing the first catalyst composition is by a redox reaction between a compound of trivalent antimony such as $Sb_2O_3$ and a compound of pentavalent vanadium such as $V_2O_5$, during which the antimony is oxidized and the vanadium reduced.

The foregoing redox reaction was described by Birchall and Sleight (*Inorganic Chem.* 15, 868-70 [1976]) and by Berry et al. (*J. Chem. Soc. Dalton Trans.*, 1983, 9-12), who effected the reaction by heating a dry mixture of the above reactants at temperatures above 600° C. This product had a tetragonal rutile-type crystalline structure with a unique x-ray diffraction pattern.

However, it has been found that the redox reaction can successfully and more conveniently be carried out in an aqueous medium by heating at a temperature of at least 80° C. and up to 200° C., for instance, by heating an aqueous dispersion of a $V^{5+}$ compound, such as $NH_4VO_3$ or $V_2O_5$, with an $Sb^{3+}$ compound, such as by reacting $Sb_2O_3$ and $NH_4VO_3$ (or $V_2O_5$). This step is followed by evaporation, drying and then calcining the product in a molecular oxygen-containing atmosphere, such as air, at from 350° to 700° or 750° C., usually 400° to 650° C. The length of the calcination period may range from 30 minutes to 12 hours, but satisfactory catalyst compositions are usually obtained by calcination at such temperatures for a period of from 1 to 5 hours.

At least part of any excess of trivalent antimony compound, such as $Sb_2O_3$, is usually oxidized to $Sb_2O_4$ during the calcination in a molecular oxygen-containing atmosphere, such as air.

The ingredients of the first catalyst composition other than vanadium and antimony (and of course part of the oxygen) suitably can be incorporated after completion of the foregoing redox reaction. Thus, the additives A, G, J and/or T, if any, can be added in the slurry after the redox reaction, or the solid particles containing the vanadium and antimony values after separation from the aqueous medium can be coated or impregnated in a known manner with such additives at any suitable stage prior to final calcination of the catalyst, by methods generally known in the art, using oxides, hydroxides, acids, salts (particularly organic salts such as acetates), and other compounds of such elements.

In formula (1) subscript a usually is at least 0.4 or 0.5. In formula (1) at least 0.2 atoms of W are usually present per atom of V, and the total of W plus Sn atoms (if any Sn is present) is usually at least 0.4 atoms. Preferred compositions of formula (1) contain at least 0.4 atoms of W per atom of V. Particularly when W is present, it is especially useful to have at least 0.4 atoms of P per atom of V in addition to the W. Especially useful are such compositions wherein said diluent/support comprises 20-100 weight percent alumina and 80 to zero weight percent silica.

Especially useful catalysts of formula (1) or (3) description are those in which a is at least 1, wherein A includes at least 1 atom of W.

Not only does the catalyst support in the first catalyst composition (formula (1) or (3)) improve mechanical stability of the catalyst, but also the catalytic activity is significantly improved, especially in the case of alumina and silica-alumina. Besides alumina and silica-alumina other supports that can be used are silica, titania, silica-titania, $Nb_2O_5$, silica-niobia, silica-zirconia, zirconia and magnesia, etc.

In the first catalyst composition (formula (1) and (3)), now preferred support materials for not only improving mechanical stability but also for improving the yield of the desired nitriles are selected from silica-alumina and alumina having 20-100, usually 50-100, preferably 60-100 weight percent alumina; silica-titania and titania having 20-100 weight percent titania; silica-zirconia and zirconia having 80-100 weight percent zirconia; and silica-niobia and niobia having 30-100 weight percent niobia ($Nb_2O_5$).

In the preparation of the second catalyst composition of formula (2) the metal oxides can be blended together or can be formed separately and then blended or formed separately or together in situ. Promoter oxides can be incorporated into the bismuth-cerium-molybdenum based catalyst by blending into the gel before calcining or by blending into the oven-dried base catalyst before calcining. A useful manner of incorporating promoter elements is by choosing a water-soluble salt of the promoter element, forming an aqueous solution of the salt, and mixing the solution with a solution or a suspension of the base elements or salts thereof. Optionally, the promoter elements can be incorporated by the use of soluble complex salts or compounds with the desired base elements which upon calcination will yield the desired ratio of the elements in the finished catalyst.

The L metals can be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one can use any compound of iron which, upon calcination, will result in the oxides. As with the other elements, water soluble salts are preferred for the ease with which they may be uniformly dispersed within the catalyst. Most preferred is ferric nitrate. Cobalt and nickel are similarly introduced.

To introduce the molybdenum component any molybdenum oxide such as the dioxide, trioxide, pentoxide or sesquioxide can be used; more preferred is hydrolyzable or decomposable molybdenum salt such as molybdenum halide. A preferred starting material is ammonium heptamolybdate.

Other variations in starting materials will suggest themselves to one skilled in the art, particularly when the preferred starting materials mentioned hereinabove are unsuited to the economics of large-scale manufacture. In general, any comounds containing the desired catalyst components may be used provided that they result, upon heating to a temperature within the range disclosed hereinafter, in the oxides of the instant catalyst.

These second catalyst compositions are conveniently prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

In the second catalyst composition the support can be any of the usual supports such as silica, alumina, silica-alumina, titania, zirconia, $Nb_2O_5$.

The catalysts of formula (1) or (3) of the present invention, and used in the process of the invention, are essentially free of uranium. Moreover, in the process of the invention, essentially no sulfur or sulfur compounds, or halogen or halogen compounds, are present in the reaction mixture during the ammoxidation.

While particulate catalytic mixtures of formula (1) or (3) and formula (2) catalysts are physical mixtures of separate particles of each catalyst, pellets or other shapes can be pressed from such particulate mixture to form larger particles for fixed bed operations, etc.

In the ammoxidation of the present invention, the reaction is carried out in the gas phase by contacting a mixture of the paraffin, ammonia, molecular oxygen, and inert diluent, if any, conveniently in a fixed bed of the catalyst mixture, or a gravity flowing bed, a fluidized bed or a fast transport reactor mode.

Examples of inert diluents useful in the reaction are $N_2$, He, $CO_2$, $H_2O$ and Ar.

The reaction temperature range can vary from 350° to 700° C., but is usually 460° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure of the reaction usually ranges from 2 to 45 psia. Most often, pressure is somewhat above atmospheric.

The following examples of the invention ar exemplary and should not be taken as in any way limiting.

EXAMPLE 1

A catalyst having the empirical formula 50 wt % $VSb_5WO_x + 50$ wt % $Al_2O_3$ support was made as follows:

In a stirred flask equipped for heating under reflux, 5.4 g $NH_4VO_3$ was dissolved in 150 ml hot water. To the hot solution 33.6 g $Sb_2O_3$ was added, and the slurry was boiled under reflux for 16–18 hours overnight. There was ammonia evolution, and the vanadium antimonate mixture turned gray-green.

In a separate operation, 59.0 g Catapal SB (hydrated alumina) was mixed with 200 ml $H_2O$ (cold) + 23.0 g acetic acid (10 percent solution) and stirred until the suspension gelled. It took about 3 hours, and the gel was soft, homogeneous, with the consistency of thick cream.

Meanwhile, the vanadium antimonate slurry was transferred to a beaker. A solution of 12.5 g ammonium meta-tungstate in about 25 ml $H_2O$ was then added, followed by the addition, with stirring (magnet) of the alumina gel. After partial evaporation, the mixture became too thick for stirring. It was then transferred to an evaporating dish, and the evaporation, following by drying overnight, was continued in an oven at 110°–120° C. The dried material was precalcined at 350° C. for 5 hours, screened to 20/35 mesh, then calcined 3 hours at 610° C.

EXAMPLE 2

A catalyst with the empirical formula 50 wt % $Bi_3Ce_2Pb_5Mo_{11}W_{1.5}O_x + 50$ wt % $SiO_2$ was made from the following components:

Ammonium heptamolybdate: 38.84 g
$Bi(NO_3)_3 \cdot 5H_2O$: 29.11 g
$Pb(NO_3)_2$: 33.12 g
$(NH_4)_2Ce(NO_3)_6$: 21.93 g
$(NH_4)_6H_2W_{12}O_{40} \cdot H_2O$ (85% $WO_3$): 8.18 g
40% $SiO_2$: 203.71 g Ammonium heptamolybdate was dissolved in ~200 ml warm distilled $H_2O$. Ammonium metatungstate was then dissolved in this solution. The silica sol (Nalco 2327, 40% $SiO_2$, ammonium stabilized) was then added to the slurry. In a separate beaker bismuth nitrate was dissolved in ~50 ml 10% nitric acid. Ceric ammonium nitrate was dissolved in this solution. It was warmed and lead nitrate was added. This solution was poured slowly with stirring into the other solution. The pH of the resulting slurry was adjusted to ~3 by the dropwise addition of concentrated ammonium hydroxide. It was then stirred and heated to remove excess $H_2O$. It was dried overnight at 120° C. The dried material was denitrified by heating at 290° C. for 3 hours and then at 425° C. for 3 hours. It was then ground and screened to 20–35 mesh particle size. The catalyst was then calcined at 650° C. for 3 hours.

EXAMPLE 3

A catalyst having the composition represented by the empirical formula 50 wt % $Bi_4Ce_4Mo_{10}W_2O_x$ and 50 wt % $SiO_2$ was made as follows:

26.48 g of ammonium heptamolybdate were dissolved in about 200 ml warm distilled water. 81.8 g ammonium metatungstate were then dissolved in this solution. 130.93 g silica sol (Nalco 2327, 40% $SiO_2$, ammonium stabilized) were added.

In a separate beaker, 29.11 g bismuth nitrate were dissolved in 50 ml of 10% nitric acid. 32.90 g ceric ammonium nitrate were then dissolved in this solution. The resulting solution was added slowly with stirring to the molybdate tungstate solution. The pH of the resulting slurry was adjusted to about 3 by the dropwise addition of concentrated ammonium hydroxide. The slurry was then heated and stirred to remove excess water. It was dried overnight at 110° C.

The dried material was denitrified by heating at 290° C. or 3 hours and then at 425° C. for 3 hours. It was ground and screened to between 20–35 mesh particle size. Final calcination was at 650° C. for 3 hours.

EXAMPLE 4

A catalyst having the empirical formula 50 wt % $VSb_{3.5}P_{0.5}WO_x + 50$ wt % $Al_2O_3$ support was made as follows:

In a stirred flask equipped for heating under reflux, 3.81 g $NH_4VO_3$ were dissolved in 90 ml hot water. To the hot solution 16.6 g $Sb_2O_3$ were added, and the slurry was boiled under reflux for 16–18 hours overnight. There was ammonia evolution, and the vanadium antimonate mixture turned gray-green.

In a separate operation, 35.3 g Catapal SB (hydrated alumina) were mixed with 127.2 ml $H_2O$ (cold) + 14.1 g acetic acid (10 percent solution) and stirred until the suspension gelled. It took about 3 hours, and the gel was soft, homogeneous, with the consistency of thick cream.

Meanwhile, the vanadium antimonate slurry was transferred to a beaker. A solution of 8.80 g ammonium meta-tungstate in about 20 ml $H_2O$ and a solution of 1.77 g $(NH_4)_2HPO_4$ in $H_2O$ were then added, followed by the addition, with stirring (magnet) of the alumina gel. After partial evaporation, the mixture became too thick for stirring. It was then transferred to an evaporating dish, and the evaporation, following by drying overnight, was continued in an oven at 110°–120° C. The dried material was precalcined at 350° C. for 5 hours, screened to 20/35 mesh, then calcined 3 hours at 610° C.

EXAMPLE 5

A catalyst having the empirical formula 50 wt % $VSb_5K_{0.2}WO_x + 50$ wt % $Al_2O_3$ support was made as follows:

In a stirred flask equipped for heating under reflux, 3.20 g $NH_4VO_3$ were dissolved in 90 ml of hot water. To the hot solution 19.90 g $Sb_2O_3$ were added, and the slurry was boiled under reflux for 16–18 hours overnight. There was ammonia evolution, and the vanadium antimonate mixture turned gray-green.

In a separate operation, 35.3 g Catapal SB (hydrated alumina) were mixed with 127.2 ml $H_2O$ (cold) + 14.1 g acetic acid (10 percent solution) and 3.8 ml of 0.1 g/ml $K_2CO_3$ solution and stirred until the suspension gelled. It took about 3 hours, and the gel was soft, homogeneous, with the consistency of thick cream.

Meanwhile, the vanadium antimonate slurry was transferred to a beaker. A solution of 7.36 g ammonium meta-tungstate in about 15 ml $H_2O$ was then added, followed by the addition, with stirring (magnet) of the alumina gel. After partial evaporation, the mixture became too thick for stirring. It was then transferred to an evaporating dish, and the evaporation, following by drying overnight, was continued in an oven at 110°-120° C. The dried material was pecalcined at 350° C. for 5 hours, screened to 20/35 mesh, then calcined 3 hours at 610° C.

EXAMPLE 6

A catalyst having the empirical formula 50 wt % $VSb_5Pb_{0.5}WO_x + 50$ wt % $Al_2O_3$ support was made as follows:

In a stirred flask equipped for heating under reflux, 2.94 g $NH_4VO_3$ were dissolved in 90 ml hot water. To the hot solution 18.30 g $Sb_2O_3$ were added, and the slurry was boiled under reflux for 16-18 hours overnight. There was ammonia evolution, and the vanadium antimonate mixture turned gray-green.

In a separate operation, 35.3 g Catapal SB (hydrated alumina) were mixed with 127.2 ml $H_2O$ (cold) + 14.1 g acetic acid (10 percent solution) and stirred until the suspension gelled. It took about 3 hours, and the gel was soft, homogeneous, with the consistency of thick cream.

Meanwhile, the vanadium antimonate slurry was transferred to a beaker. A solution of 6.77 g ammonium meta-tungstate in about 15 ml $H_2O$ and a solution of 4.76 g $Pb(OAc)_2.3H_2O$ in $H_2O$ were then added, followed by the addition, with stirring (magnet) of the alumina gel. After partial evaporation, the mixture became too thick for stirring. It was then transferred to an evaporating dish, and the evaporation, following by drying overnight, was continued in an oven at 110°-120° C. The dried material was precalcined at 350° C. for 5 hours, screened to 20/35 mesh, then calcined 3 hours at 610° C.

EXAMPLE 7

A catalyst having the empirical formula 47 wt % $VSb_5WO_x + 50$ wt % $Al_2O_3/3$ wt % $Nb_2O_5$ support was made as follows:

In a stirred flask equipped for heating under reflux, 5.4 g $NH_4VO_3$ were dissolved in 150 ml hot water. To the hot solution 33.6 g $Sb_2O_3$ were added, and the slurry was boiled under reflux for 16-18 hours overnight. There was ammonia evolution, and the vanadium antimonate mixture turned gray-green.

Meanwhile, the vanadium antimonate slurry was transferred to a beaker. A solution of 12.5 g ammonium meta-tungstate in about 25 ml $H_2O$ was then added. 7.34 g $Nb(OEt)_5$ was added dropwise wit good agitation. After evaporation, the material was dried overnight in an oven at 110°-120° C. The dried material was ground and thoroughly mixed with 53.5 g Catapal SB. The mixture was kneaded to a paste with a solution of 6 ml glacial acetic acid in 57 ml $H_2O$. Additional $H_2O$ had to be added. The paste was dried again at 110°-120° C. overnight. This dried material was precalcined at 350° C. for 2.5 hours, and at 420° C. for 2.5 hours screened to 20/35 mesh, then calcined 3 hours at 610° C.

EXAMPLE 8

A catalyst was made having the empirical composition, 50 wt % $Bi_{6.8}Ce_{1.2}Mo_{12}O_x + 50$ wt % $SiO_2$, as follows: 41.23 g of bismuth nitrate were dissolved in 50 ml of dilute (10%) nitric acid. 8.22 g of ceric ammonium nitrate were dissolved in the bismuth nitrate solution.

In a separate step 26.48 g of ammonium heptamolybdate were dissolved in 50 ml of water. To this solution were added 109.64 g of 40 wt% silica sol, ammonium stabilized. The nitrate solution was then slowly added to this mixture with constant stirring with a magnetic stirrer. The resulting mixture was heated to approximately 80° C. and evaporated to dryness with constant stirring. The resulting mass was further dried in an oven at about 120° C. for 16 hours. The dried material was heat treated in air at 290° C. for 3 hours, 425° C. for 3 hours, and finally at 550° C. for 16 hours.

EXAMPLE 9

A catalyst was made having the empirical composition, 80 wt% $Bi_2Ce_6Mo_{12}O_x + 20$ wt% $SiO_2$, as follows: 19.40 g bismuth nitrate were dissolved in 50 ml of dilute (10%) nitric acid. 65.79 g of ceric ammonium nitrate were dissolved in the bismuth nitrate solution.

In a separate step 42.38 g of ammonium heptamolybdate were dissolved in about 100 ml of water. To this solution were added 39.72 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 10

A catalyst was made having the empirical composition, 80 wt% $K_{0.05}Cs_{0.02}Bi_4Ce_4Mo_{12.03}O_x + 20$ wt% $SiO_2$ as follows: 38.81 g of bismuth nitrate were dissolved in 50 ml of dilute (10%) nitric acid. 43.86 g of ceric ammonium nitrate were dissolved in the bismuth nitrate solution. To this solution were added 1.0 g of a 10 wt% $KNO_3$ solution and 0.78 g of a 10 wt% $CsNO_3$ solution.

In a separate step 42.48 g of ammonium heptamolybdate were dissolved in about 100 ml of water. To this solution were added 41.56 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 11

A catalyst was made having the empirical composition, 80 wt% $Bi_4Ce_4Mo10W_2O_x + 20$ wt% $SiO_2$, as follows: 38.81 g of bismuth nitrate were dissolved in 50 ml of dilute (10%) nitric acid. 43.86 g of ceric ammonium nitrate were dissolved in the bismuth nitrate solution.

In a separate step 35.31 g of ammonium heptamolybdate and 9.86 g of ammonium metatungstate (85 wt% $WO_3$ equivalent) were dissolved in about 100 ml of water. To this solution were added 43.64 g of 40% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 12

A catalyst was made having the empirical composition, 80 wt% $Tl_{0.03}Bi_4Ce_4Mo_{12}O_x$+20 wt% $SiO_2$ as follows: 38.81 g of bismuth nitrate were dissolved in 50 ml of dilute (10%) nitric acid. 43.86 g of ceric ammonium nitrate and 0.16 g of thallous nitrate were dissolved in the bismuth nitrate solution.

In a separate step 42.38 g of ammonium heptamolybdate were dissolved in about 100 ml of water. To this solution were added 41.53 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 13

A catalyst was made having the empirical composition, 80 wt% $Cs_{0.02}Bi_4Ce_4Mo_{12.01}O_x$+20 wt% $SiO_2$ as follows: 38.81 g of bismuth nitrate were dissolved in 50 ml of dilute (10%) $HNO_3$. 43.86 grams of ceric ammonium nitrate were dissolved in the bismuth nitrate solution along with 0.40 g of a 10 wt% $CsNO_3$ solution. In a separate step 42.41 g of ammonium heptamolybdate were dissolved in about 100 ml of water. To this solution were added 41.49 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 14

A catalyst was made having the empirical composition, 80 wt% $Bi_7Ce_1Mo_{10}W_2O_x$+20 wt% $SiO_2$ as follows: 67.91 g of bismuth nitrate were dissolved 50 ml of dilute (10%) nitric acid. 10.96 g of ceric ammonium nitrate were dissolved in the bismuth nitrate solution.

In a separate step 35.31 g of ammonium heptamolybdate and 10.91 g of ammonium metatungstate (85 wt% $WO_3$ equivalent) were dissolved in about 100 ml of water. To this solution were added 46.23 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, and finally at 550° C. for 16 hours.

EXAMPLE 15

A catalyst was made having the empirical composition, 80 wt% $Cr_2Ce_2Bi_4Mo_{12}O_x$+20 wt% $SiO_2$ as follows: 38.81 g of bismuth nitrate were dissolved in 50 ml of dilute (10%) nitric acid. 21.93 g of ceric ammonium nitrate and 16.01 g of chromium nitrate were dissolved in the bismuth nitrate solution.

In a separate step 42.38 g of ammonium heptamolybdate were dissolved in about 100 ml of water. To this solution were added 39.24 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 16

A catalyst was made having the empirical composition, 80 wt% $Te_2Ce_2Bi_4Mo_{12}O_x$+20 wt% $SiO_2$, as follows: 38.81 g of bismuth nitrate were dissolved in 50 ml of dilute (10%) nitric acid. 21.93 g of ceric ammonium nitrate were dissolved in the bismuth nitrate solution.

In a separate step 42.38 g of ammonium heptamolybdate were dissolved in about 150 ml of water. 9.19 g of $H_2TeO_4.H_2O$ were added to the solution along with 100 ml of water. Enough ammonium hydroxide was added to get all the telluric acid into solution. To this solution were added 41.33 g of 40 wt% silica sol, ammonium stabilized. The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 17

A catalyst was made having the empirical composition, 50 wt% $Bi_4Ce_4Sb_1Mo_{10}W_2O_x$+50 wt% $SiO_2$, as follows: 29.11 g of bismuth nitrate were dissolved in 50 ml of dilute (10%) nitric acid. 32.89 g of ceric ammonium nitrate were dissolved in the bismuth nitrate solution.

In a separate step 26.48 g of ammonium heptamolybdate and 8.18 g of ammonium metatungstate (85 wt% $WO_3$ equivalent) were dissolved in about 100 ml of water. To this solution were added 2.19 g of antimony trioxide followed by 39.24 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 650° C. for 3 hours.

EXAMPLE 18

A catalyst was made having the empirical composition, 80 wt% $Bi_4Ce_4Fe_{0.05}Sb_1Mo_{10}W_2O_x + 20$ wt% $SiO_2$, as follows: 38.81 g of bismuth nitrate were dissolved in 50 ml of dilute (10%) nitric acid. 43.86 g of ceric ammonium nitrate and 4.04 g of ferric nitrate were dissolved in the bismuth nitrate solution.

In a separate step 35.31 g of ammonium heptamolybdate and 10.91 g of ammonium metatungstate (85 wt% $WO_3$ equivalent) were dissolved in about 100 ml of water. To this solution were added 2.92 g of antimony trioxide followed by 45.97 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 19

A catalyst was made having the empirical composition, 80 wt% $Bi_4Ce_4Mn_1Sb_1Mo_{10}W_2O_x + 20$ wt% $SiO_2$, as follows: 38.81 g of bismuth nitrate were dissolved in 50 ml of dilute (10%) nitric acid. 43.86 g of ceric ammonium nitrate and 6.99 g of a 51.2 wt% manganous nitrate solution were dissolved in the bismuth nitrate solution.

In a separate step 35.31 g of ammonium heptamolybdate and 10.91 g of ammonium metatungstate (85 wt% $WO_3$ equivalent) were dissolved in about 100 ml of water. To this solution were added 2.92 g of antimony trioxide followed by 46.35 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 20

A catalyst was made having the empirical composition, 80 wt% $Bi_4Ce_4V_{0.5}Mg_{0.5}Sb_1Mo_{10}W_2O_x + 20$ wt% $SiO_2$, as follows: 38.81 g of bismuth nitrate were dissolved in 50 ml of dilute (10%) nitric acid. 43.86 g of ceric ammonium and 2.56 g of magnesium nitrate were dissolved in the bismuth nitrate solution.

In a separate step 35.31 g of ammonium heptamolybdate, 10.91 g of ammonium metatungstate (85 wt% $WO_3$ equivalent), and 1.17 g of ammonium metavanadate were dissolved in about 150 ml of water along with sufficient ammonium hydroxide to effect complete dissolution. To this solution were added 2.92 g of antimony trioxide followed by 46.30 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 21

A catalyst was made having the empirical composition, 50 wt% $Bi_4Ce_4Sb_1Mo_8W_2O_x + 50$ wt% $SiO_2$, as follows: 29.19 g of bismuth nitrate were dissolved in 50 ml of dilute (10%) nitric acid. 32.89 g of ceric ammonium nitrate were dissolved in the bismuth nitrate solution.

In a separate step 21.19 g of ammonium heptamolybdate and 8.18 g of ammonium metatungstate (85 wt% $WO_3$ equivalent) were dissolved in about 150 ml of water along with sufficient ammonium hydroxide to effect complete dissolution. To this solution were added 2.19 g of antimony trioxide followed by 125.60 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 650° C. for 3 hours.

EXAMPLE 22

A catalyst was made having the empirical composition, 80 wt% $Bi_3Ce_3Pb_3Sb_1Mo_{10}W_2O_x + 20$ wt% $SiO_2$, as follows: 29.11 g of bismuth nitrate were dissolved in 50 ml of dilute (10%) nitric acid. 32.89 g of ceric ammonium nitrate and 19.87 g of lead nitrate were dissolved in the bismuth nitrate solution.

In a separate step 35.51 g of ammonium heptamolybdate and 10.91 g of ammonium metatungstate (85 wt% $WO_3$ equivalent) were dissolved in about 100 ml of water along with sufficient ammonium hydroxide to effect complete dissolution. To this solution were added 2.92 g of antimony trioxide followed by 48.87 g of 40 wt% silica sol (Nalco 2327). The nitrate solution was then slowly added to the this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 23

A catalyst was made having the empirical composition, 80 wt% $Bi_{3.5}Ce_{3.5}Cr_1Mo_{12}O_x + 20$ wt% $SiO_2$, as follows: 29.11 g of bismuth nitrate were dissolved in 50 ml of dilute (10%) nitric acid. 32.89 g of ceric ammonium nitrate and 16.01 g of chromium nitrate were dissolved in the bismuth nitrate solution.

In a separate step 42.37 g of ammonium heptamolybdate were dissolved in about 100 ml of water. To this solution were added 38.38 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 24

A catalyst was made have the empirical composition, 80 wt% $La_2Ce_2Bi_4Mo_{12}O_x$ + 20 wt% $SiO_2$, as follows: 38.81 g of bismuth nitrate were dissolved in 50 ml of dilute (10%) nitric acid. 21.93 g of ceric ammonium nitrate and 15.88 g of lanthanum nitrate were dissolved in the bismuth nitrate solution.

In a separate step 42.38 g of ammonium heptamolybdate were dissolved in about 100 ml of water. To this solution were added 41.41 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 25

A catalyst was made having the empirical composition, 80 wt% $Y_2Ce_2Bi_4Mo_{12}O_x$ + 20 wt% $SiO_2$, as follows: 38.81 g of bismuth nitrate were dissolved in 50 ml of dilute (10%) nitric acid. 21.93 g of ceric ammonium nitrate and 14.60 g of yttrium nitrate were dissolved in the bismuth nitrate solution.

In a separate step 42.38 g of ammonium heptamolybdate were dissolved in about 100 ml of water. To this solution were added 40.17 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 26

A catalyst was made having the empirical composition, 80 wt% $K_{0.1}Pr_2Ce_2Bi_4Mo_{12.05}O_x$ + 20 wt% $SiO_2$, as follows: 38.81 g of bismuth nitrate were dissolved in 50 ml of dilute (10%) nitric acid. 21.93 g of ceric ammonium nitrate and 16.68 g of praseodymium nitrate were dissolved in the bismuth nitrate solution. To this solution were added 2.00 g of a 10 wt% solution of $KNO_3$.

In a separate step 42.55 g of ammonium heptamolybdate were dissolved in about 100 ml of water. To this solution were added 41.61 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 27

A catalyst was made having the empirical composition, 80 wt% $K_{0.1}Nd_2Ce_2Bi_4Mo_{12.05}O_x$ + 20 wt% $SiO_2$, as follows: 38.81 g of bismuth nitrate were dissolved in 50 ml of dilute (10%) nitric acid. 21.93 g of ceric ammonium nitrate and 17.53 g of neodymium nitrate were dissolved in the bismuth nitrate solution. To this solution were added 2.02 g of a 10 wt% solution of $KNO_3$.

In a separate step 42.55 g of ammonium heptamolybdate were dissolved in about 100 ml of water. To this solution were added 41.70 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° C. for 3 hours, and finally at 550° C. for 16 hours.

EXAMPLE 28

A catalyst was made having the empirical composition, 80 wt% $K_{0.01}Di_2Ce_2Bi_4Mo_{12.03}O_x$ + 20 wt% $SiO_2$, as follows: 38.81 g of bismuth nitrate were dissolved in 50 ml of dilute (10%) nitric acid. 21.93 g of ceric ammonium nitrate and 15.88 g of didymium nitrate were dissolved in the bismuth nitrate solution. To this solution were added 2.00 g of a 10 wt% solution of $KNO_3$.

In a separate step 42.55 g of ammonium heptamolybdate were dissolved in about 100 ml of water. To this solution were added 41.56 g of 40 wt% silica sol (Nalco 2327). The nitrate solution was then slowly added to this mixture with constant stirring. The pH of the mixture was adjusted to about 3.0 by the dropwise addition of a concentrated ammonium hydroxide solution. The mixture was refluxed for 3 hours. Additional water was added to the slurry as necessary to keep the mixture stirring. The slurry was then evaporated to dryness and the resulting mass was further dried in an oven at about 120° C. for 16 hours. The dried material was heat treated in air at 290° C. for 3 hours, 425° for 3 hours, and finally at 550° C. for 16 hours.

In the ammoxidation runs of the following examples, the catalyst, or the mixture of catalysts, is in a tubular $\frac{3}{8}$ inch I.D. stainless steel fixed bed reactor. When a mixture of particulate catalysts is used, as in the invention examples, the desired weight of each of the two catalyst compositions is put in a vial and shaken until uniformly dispersed before placing the desired amount of the catalyst mixture in the reaction tube. The reactor is equipped with a preheat leg immersed in a temperature controlled molten salt bath. The feed is fed to the catalyst for one hour before the runs are started; the runs of each example last 30 minutes.

EXAMPLE 29

A catalyst having the empirical composition 50 wt % $VSbPWO_x$—50 wt % $Al_2O_3$ was made as follows:

Ammonium meta-vanadate (5.48 g) and ammonium meta-tungstate (12.64 g) were dissolved in ~100 cc of hot water. 85% phosphoric acid (5.34 g) was then added to the above solution along with an additional 20–30 cc of water, turning the solution from yellow to a deep burgundy red. While rapidly stirring the red solution from about, antimony trioxode (6.75 g) was added, resulting in an initial red/orange slurry. This slurry was covered and allowed to "reflux" for one hour after which the color changed to a dark blue/green.

In a separate beaker, Catapal SB Al$_2$O$_3$ (29.41 g=25.0 g Al$_2$O$_3$) was slurried in 100 cc H$_2$O and peptized with glacial acetic acid (4.2 g) to form a sol-like dispersed alumina. After aging for 1 hour, this dispersion was slowly added to the blue/green slurry from above along with enough water to prevent the slurry from gelling up (~100 cc). The resulting blue/green slurry was then evaporated to near dryness on a hot plate, and the thick bluish paste obtained was further dried at 110° C. for ~16 hrs. A heat treatment of 350° C. for 5 hours was carried out on the dried catalyst precursor, followed by crushing and screening to +20–35 mesh particles. A portion of the sieved materials was then subjected to a final calcination of 610° C. for 3 hours.

EXAMPLE 30

A catalyst having the empirical composition 50 wt % VSb$_{0.5}$PWO$_x$—50 wt % Al$_2$O$_3$ was made exactly as in Example 29 but using the following amounts of the batch materials:

NH$_4$VO$_3$: 7.16 g
"WO$_3$": 16.70 g
85% H$_3$PO$_4$: 7.06 g
Sb$_2$O$_3$: 0.89 g
Al$_2$O$_3$ (catapal SB alumina): 29.41 g

EXAMPLE 31

A catalyst having the empircal composition 25 wt% VPWO$_x$—75 wt% Al$_2$O$_3$ was made as in Example 29, but using the amounts of the batch materials shown below, including oxalic acid, which was added to the vanadium, phosphorus and tungsten containing solution to form a solution also containing antimony (instead of the slurry of Example 1).

NH$_4$VO$_3$: 3.75 g
"WO$_3$": 8.66 g
85% H$_3$PO$_4$: 3.66 g
oxalic acid: 8.0 g
Al$_2$O$_3$ (Catapal SB): 44.12 g

EXAMPLE 32

A catalyst having the empirical composition 50 wt% Bi$_4$Ce$_4$Mo$_{10}$W$_2$O$_x$+50 wt% SiO$_2$ was made as follows:

1765.65 g of (NH$_4$)$_6$Mo$_7$O$_{24}$.4H$_2$O were dissolved in 2000 ml warm water. 545.7 g (NH$_4$)$_6$H$_2$W$_{12}$O$_{40}$.H$_2$O—85% WO$_3$—were dissolved with the addition more H$_2$O, to make a solution of 4750 ml. A 40 wt % SiO$_2$ sol (NH$_3$ stabilized) was added in the amount of 8728.75 g.

In a separate beaker, 1940.4 g Bi(NO$_3$)$_3$.5H$_2$O were dissolved in a mixture of 47.5 ml conc. HNO$_3$ and 250 ml H$_2$O. 2193.04 g (NH$_4$)$_2$Ce(NO$_3$)$_6$ were then dissolved in the solution. The resulting solution was added slowly with stirring to the molybdate tungstate silica solution. The pH of the resulting slurry was adjusted to about 3 by the addition of about 1500 ml of concentrated ammonium hydroxide. A portion of this slurry was then heated and stirred to remove excess water. It was dried overnight at 110° C.

The dried material was denitrified by heating at 290° C. or 3 hours and then at 425° C. for 3 hours. It was ground and screened to between 20–35 mesh particle size. Final calcinationw as at 650° C. for 3 hours.

EXAMPLE 33

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 1.9. Water was introduced through a septum at the top of the preheat leg, using a syringe pump. The reaction temperature was 500° C. and the molar feed ratios were 8 propane/1.1NH$_3$/2.1O$_2$/1H$_2$O. The contact time was 0.4 seconds. Analysis of the reactor effluent showed that propane conversion was 11.9 percent; yield and selectivity of propane to acrylonitrile were 3.1 and 26.1, respectively; yield and selectivity to HCN were 0.6 and 5.1, respectively; yield and selectivity to propylene were 5.3 and 44.7, respectively.

COMPARATIVE EXAMPLE A

In this example the gaseous feed components were metered through mass flow controllers into the bottom of the reactor through the preheat leg. Water was introduced through a septum at the top of the preheat leg, using a syringe pump. The reaction temperature was 500° C. and the molar feed ratios were 8 propane/1.1NH$_3$/2.1O$_2$/1H$_2$O. The catalyst was the catalyst of Example 1 alone. The contact time was 0.2 seconds. Analysis of the reactor effluent showed that propane conversion was 13.5 percent; yield and selectivity of propane to acrylonitrile were 1.7 and 12.7, respectively; yield and selectivity to HCN were 0.8 and 5.7, respectively; yield and selectivity to propylene were 7.8 and 58.1, respectively.

Even though Example 33 gave a somewhat lower conversion of propane, note that when compared to this example the yield and selectivity to acrylonitrile were higher and the yield and selectivity to propylene were desirably lower.

EXAMPLE 34

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.95. Water was introduced through a septum at the top of the preheat leg, using a syringe pump. The reaction temperature was 500° C. and the molar feed ratios were 8 propane/1.1NH$_3$/2.1O$_2$/1H$_2$O. The contact time was 0.6 seconds. Analysis of the reactor effluent showed that propane conversion was 10.9 percent; yield and selectivity of propane to acrylonitrile were 3.6 and 33.2, respectively; yield and selectivity to HCN were 0.6 and 5.2, respectively; yield and selectivity to propylene were 4.2 and 38.6, respectively.

EXAMPLE 35

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.48. Water was introduced through a septum at the top of the preheat leg, using a syringe pump. The reaction temperature was 500° C and the molar feed ratios were 8 propane/1.1NH$_3$/2.1O$_2$/1H$_2$O. The contact time was 1.0 seconds. Analysis of the reactor effluent showed that propane conversion was 9.9 percent; yield and selectivity of propane to acrylonitrile were 3.6 and 36.8, respectively; yield and selectivity to HCN were 0.4 and 4.3 respectively; yield and selectivity to propylene were 3.3 and 33.3, respectively.

EXAMPLE 36

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.48. Water was introduced through a septum at the top of the preheat leg, using a syringe pump. The reaction temperature was 500° C. and the molar feed ratios were 8 propane/$1.1NH_3$/$3.0O_2$/$1.1H_2O$. The contact time was 1.0 seconds. Analysis of the reactor effluent showed that propane conversion was 13.5 percent; yield and selectivity of propane to acrylonitrile were 5.4 and 39.7, respectively; yield and selectivity to HCN were 0.6 and 4.6, respectively; yield and selectivity to propylene were 3.0 and 22.7, respectively. This example shows the favorable effect, compared to Example 35, of an increased oxygen to propane ratio.

COMPARATIVE EXAMPLE B

In this example the gaseous feed components were metered through mass flow controllers into the bottom of the reactor through the preheat leg. The catalyst was a mixture of the catalyst of Example 1 and a prior art catalyst for the ammoxidation of propylene having the composition 50% $Cs_{0.05}K_{0.1}Ni_{2.5}Co_{4.5}MnFe_2BiCr_{0.5}Mo_{13.2}O_x$+50% $SiO_2$ support. The weight ratio of the former to the latter was 0.11. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 2.0 seconds. Analysis of the reactor effluent showed that propane conversion was 6.7 percent; yield and selectivity of propane to acrylonitrile were 0.9 and 13.8, respectively; yield and selectivity to HCN were 0.1 and 1.0, respectively; yield and selectivity to propylene were 2.6 and 39.2, respectively. The run shows the effect of using a co-catalyst outside of the invention.

EXAMPLE 37

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.21. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 2.0 seconds. Analysis of the reactor effluent showed that propane conversion was 9.2 percent; yield and selectivity of propane to acrylonitrile were 4.8 and 52.1, respectively; yield and selectivity to HCN were 0.3 and 3.6, respectively; yield and selectivity to propylene were 1.6 and 16.9, respectively.

EXAMPLE 38

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.21. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 2.2 seconds. Analysis of the reactor effluent showed that propane conversion was 8.6 percent; yield and selectivity of propane to acrylonitrile were 4.4 and 51.1, respectively; yield and selectivity to HCN were 0.4 and 4.0, respectively; yield and selectivity to propylene were 1.6 and 18.5, respectively.

EXAMPLE 39

In this example the gaseous feed components were metered through mass flow controllers into the bottom of the reactor through the preheat leg. The catalyst was a mixture of the catalyst of Example 1 and the catalyst of Example 3 in the weight ratio of the former to the latter of 0.10. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 4.0 seconds. Analysis of the reactor effluent showed that propane conversion was 8.3 percent; yield and selectivity of propane to acrylonitrile were 4.9 and 59.2, respectively; yield and selectivity to HCN were 0.3 and 3.1, respectively; yield and selectivity to propylene were 0.8 and 9.2, respectively.

EXAMPLE 40

In this example the gaseous feed components were metered through mass flow controllers into the bottom of the reactor through the preheat leg. The catalyst was the catalyst of Example 1 and the catalyst of Example 3 in the weight ratio of the former to the latter of 0.10. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 2.4 seconds. Analysis of the reactor effluent showed that propane conversion was 7.3 percent; yield and selectivity of propane to acrylonitrile were 4.3 and 58.2, respectively; yield and selectivity to HCN were 0.4 and 4.9, respectively; yield and selectivity to propylene were 0.5 and 6.8, respectively.

Compared with Example 10, this example shows that a shorter contact time sacrifices little in selectivity to acrylonitrile and results in less propylene per mole of converted propane.

COMPARATIVE EXAMPLE C

In this example the gaseous feed components were metered through mass flow controllers into the bottom of the reactor through the preheat leg. The catalyst was the catalyst of Example 3 above. Water was introduced through a septum at the top of the preheat leg, using a syringe pump. The reaction temperature was 500° C. and the molar feed ratios were 8 propane/$1.1NH_3$/$2.1O_2$/$1H_2O$. The contact time was 3.8 seconds. Analysis of the reactor effluent showed that propane conversion was only 2.8 percent; yield and selectivity of propane to acrylonitrile were 1.7 and 60.5, respectively; yield and selectivity to HCN were 0.2 and 6.4, respectively; yield and selectivity to propylene were 0.0 and 0.0, respectively. This catalyst provides for little propane conversion when used alone.

EXAMPLE 41

In this example the gaseous feed components were metered through mass flow controllers into the bottom of the reactor through the preheat leg. The catalyst was a mixture of the catalyst of Example 1 and the catalyst of Example 2 in the weight ratio of the former to the latter of 0.064. Water was introduced through a septum a the top of the preheat leg, using a syringe pump. The reaction temperature was 500° C. and the molar feed ratios were 8 propane/1.1NH$_3$/2.1O$_2$/1H$_2$O. The contact time was 4.0 seconds. Analysis of the reactor effluent showed that propane conversion was 7.6 percent; yield and selectivity of propane to acrylonitrile were 4.0 and 52.8, respectively; yield and selectivity to HCN were 0.2 and 2.3, respectively; yield and selectivity to propylene were 0.7 and 9.6, respectively.

EXAMPLE 42

The gaseous feed components were metered through mass flow controllers into the bottom of the reactor through the preheat leg. The catalyst was a mixture of the catalyst of Example 4 and the catalyst of Example 3 in the weight ratio of the former to the latter of 0.15. Water was introduced through a septum at the top of the preheat leg, using a syringe pump. The reaction temperature was 470° C. and the molar feed ratios 5 propane/1NH$_3$/2O$_2$/1H$_2$O. The contact time was 2.0 seconds. Analysis of the reactor effluent showed that propane conversion was 13.7 percent; yield and selectivity of propane to acrylonitrile were 8.4 and 61.1, respectively; selectivity to propylene was 9.0, all over 2 hours. After 23 hours results were essentially identical to slightly improved.

COMPARATIVE EXAMPLE D

The gaseous feed components were metered through mass flow controllers into the bottom of the reactor through the preheat leg. The catalyst was the catalyst of Example 4 alone Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of reactor effluent showed that propane conversion was 18.3 percent; yield and selectivity of propane to acrylonitrile were 3.7 and 20.4, respectively; selectivity to propylene was 52.8.

EXAMPLE 43

The gaseous feed components were metered through mass flow controllers into the bottom of the reactor through the preheat leg. The catalyst was a mixture of the catalyst of Example 5 and the catalyst of Example 3 in the weight ratio of the former to the latter of 0.20. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.2 seconds. Analysis of the reactor effluent showed that propane conversion was 12.4 percent; yield and selectivity of propane to acrylonitrile were 7.3 and 58.6, respectively; selectivity to propylene was 10.0.

COMPARATIVE EXAMPLE E

The gaseous feed components were metered through mass flow controllers into the bottom of the reactor through the preheat leg. The catalyst was the catalyst of Example 5 alone. Water was introduced through a septum at the top of the preheat leg, using a syringe pump. The reaction temperature was 470° C. and the molar fed ratios were 5 propane/1NH$_3$/2O$_2$/1H$_2$O. The contact time was 0.3 seconds. Analysis of the reactor effluent showed that propane conversion was 14.3 percent; yield and selectivity of propane to acrylonitrile were 2.4 and 17.0, respectively; selectivity to propylene was 56.0%.

EXAMPLE 44

The gaseous feed components were metered through mass flow controllers into the bottom of the reactor through the preheat leg. The catalyst was a mixture of the catalyst of Example 6 and the catalyst of Example 3 in the weight ratio of the former to the latter of 0.20. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.2 seconds. Analysis of the reactor effluent showed that propane conversion was 10.5 percent; yield and selectivity of propane to acrylonitrile were 6.0 and 57.3, respectively; selectivity to propylene was 11.0%.

COMPARATIVE EXAMPLE F

The gaseous feed components were metered through mass flow controllers into the bottom of the reactor through the preheat leg. The catalyst was the catalyst of Example 6 alone. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.2 seconds. Analysis of the reactor effluent showed that propane conversion was 11.9 percent; yield and selectivity of propane to acrylonitrile were 1.5 and 12.9, respectively; selectivity to propylene was 61.0%.

EXAMPLE 45

The gaseous feed components were metered through mass flow controllers into the bottom of the reactor through the preheat leg. The catalyst was a mixture of the catalyst of Example 7 and the catalyst of Example 3 in the weight ratio of the former to the latter of 0.20. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.1 seconds. Analysis of the reactor effluent showed that propane conversion was 15.0 percent; yield and selectivity of propane to acrylonitrile were 8.7 and 58.0, respectively; selectivity to propylene was 13.4%.

COMPARATIVE EXAMPLE G

The gaseous feed components were metered through mass flow controllers into the bottom of the reactor through the preheat leg. The catalyst was the catalyst of Example 7 alone. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.4 seconds. Analysis of the reactor effluent showed that propane conversion was 13.1 percent; yield and selectivity of propane to acrylonitrile were 2.2 and 16.6, respectively; selectivity to propylene was 60.0%.

EXAMPLE 46

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.20. Water was introduced through a septum at the top of the preheat leg, using a syringe pump. The reaction temperature was 450° C. and the molar feed ratios were 5 propane/1$NH_3$/2$O_2$/7.3$N_2$/1$H_2O$. The contact time was 3.7 seconds. Analysis of the reactor effluent showed that propane conversion was 14.5 percent; yield and selectivity of propane to acrylonitrile were 8.5 and 58.4, respectively; selectivity to propylene was 10.8%.

EXAMPLE 47

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.20. Water was introduced through a septum at the top of the preheat leg, using a syringe pump. The reaction temperature was 470° C. and the molar feed ratios were 5 propane/1$NH_3$/2$O_2$/7.3$NH_2$/1$H_2O$. The contact time was 3.6 seconds. Analysis of the reactor effluent showed that propane conversion was 13.6 percent; yield and selectivity of propane to acrylonitrile were 8.4 and 61.8, respectively; selectivity to propylene was 8.8%.

EXAMPLE 48

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.20. Water was introduced through a septum at the top of the preheat leg, using a syringe pump. The reaction temperature was 450° C. and the molar feed ratios were 5 propane/1$NH_3$/2$O_2$/1$H_2O$. The contact time was 1.9 seconds. Analysis of the reactor effluent showed that propane conversion was 12.4 percent; yield and selectivity of propane to acrylonitrile were 6.7 and 54.2, respectively; selectivity to propylene was 15.2%.

EXAMPLE 49

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.20. Water was introduced through a septum at the top of the preheat leg, using a syringe pump. The reaction temperature was 470° C. and the molar feed ratios were 5 propane/1$NH_3$/2$O_2$/1$H_2O$. The contact time was 1.9 seconds. Analysis of the reactor effluent showed that propane conversion was 14.7 percent; yield and selectivity of propane to acrylonitrile were 8.9 and 60.5, respectively; selectivity to propylene was 9.0%.

EXAMPLE 50

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.09. Water was introduced through a septum at the top of the preheat leg, using a syringe pump. The reaction temperature was 450° C. and the molar feed ratios were 3 propane/1$NH_3$/2$O_2$/7.3$N_2$/1$H_2O$. The contact time was 3.4 seconds. Analysis of the reactor effluent showed that propane conversion was 10.4 percent; yield and selectivity of propane to acrylonitrile were 6.3 and 61.0, respectively; selectivity to propylene was 9.3%.

EXAMPLE 51

The gaseous feed components were metered through mass flow controllers into the bottom of the reactor through the preheat leg. The catalyst was a mixture of the catalyst of Example 1 and the catalyst of Example 3 in the weight ratio of the former to the latter of 0.09. Water was introduced through a septum at the top of the preheat leg, using a syringe pump. The reaction temperature was 470° C. and the molar feed ratios were 3 propane/1$NH_3$/2$O_2$/7.3$N_2$/1$H_2O$. The contact time was 3.3 seconds. Analysis of the reactor effluent showed that propane conversion was 13.1 percent; yield and selectivity of propane to acrylonitrile were 8.2%, and 62.5%, respectively; selectivity to propylene was 5.5%. The productivity was 0.026 lbs of acrylonitrile per pound of catalyst mixture per hour.

When Example 51 was repeated exactly, except that the molar ratios were 1 propane/1$NH_3$/2$O_2$/7.3$N_2$/1$H_2O$, the propane conversion was 17.7 percent; yield and selectivity of propane to acrylonitrile were 9.8% and 55.2%; selectivity to propylene was 7.4%. Productivity was 0.012 lbs acrylonitrile per lb. of catalyst per hour.

COMPARATIVE EXAMPLE H

The gaseous feed components were metered through mass flow controllers into the bottom of the reactor through the preheat leg. The catalyst was a mixture of the catalyst of Example 1 and the catalyst of Example 3 in the weight ratio of the former to the latter of about 0.75. Water was introduced through a septum at the top of the preheat leg, using a syringe pump. The reaction temperature was 500° C. and the molar feed ratios were 1 propane/2$NH_3$/3$O_2$/6.9$N_2$/1$H_2O$. The contact time was 3.4 seconds. Analysis of the reactor effluent showed that propane conversion was 78.3 percent; yield and selectivity of propane to acrylonitrile were 26.5 and 33.9, respectively; selectivity to propylene was 3.8%, data taken after 1 hour. Results after 24 hours were propane conversion 80.6 percent; yield and selectivity of propane to acrylonitrile 30.7 and 38.0, respectively; selectivity to propylene 4.2%. This example illustrates the importance of a stoichiometric excess as set forth herein of paraffin to both $O_2$ and $NH_3$ in the feed to the reaction zone, ultimate yields to acrylonitrile being too low for serious industrial consideration.

EXAMPLE 52

The gaseous feed components were metered through mass flow controllers into the bottom of the reactor through the preheat leg. The catalyst is a mixture of the catalyst of Example 5 and the catalyst of Example 8 in the weight ratio of the former to the latter of 0.15. Water is introduced through a septum at the top of the preheat leg, using a syringe pump. The reaction temperature is 470° C. and the molar feed ratios are 5 propane/1$NH_3$/2$O_2$/1$H_2O$. The contact time is 2.2 seconds. Results similar to Example 42 are obtained, selectivity and yield to acrylonitrile being several times that of the yield and selectivity to propylene.

EXAMPLE 53

The gaseous feed components are metered through 5 mass flow controllers into the bottom of the reactor through the preheat leg. The catalyst is a mixture of the catalyst of Example 1 and the catalyst of Example 9 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 54

The gaseous feed components are metered through mass flow controllers into the bottom of the reactor through the preheat leg. The catalyst is a mixture of the catalyst of Example 4 and the catalyst of Example 10 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 55

The gaseous feed components are metered through mass flow controllers into the bottom of the reactor through the preheat leg. The catalyst is a mixture of the catalyst of Example 4 and the catalyst of Example 11 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 56

The gaseous feed components are metered through mass flow controllers into the bottom of the reactor through the preheat leg. The catalyst is a mixture of the catalyst of Example 7 and the catalyst of Example 12 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results. Similar to Example 42 are obtained, selectivity and yield to acrylonitrile being several times that of the yield and selectivity to propylene.

EXAMPLE 57

The gaseous feed components are metered through mass flow controllers into the bottom of the reactor through the preheat leg. The catalyst is a mixture of the catalyst of Example 7 and the catalyst of Example 13 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 58

The gaseous feed components are metered through mass flow controllers into the bottom of the reactor through the preheat leg. The catalyst is a mixture of the catalyst of Example 6 and the catalyst of Example 14 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 59

The gaseous feed components are metered through mass flow controllers into the bottom of the reactor through the preheat leg. The catalyst is a mixture of the catalyst of Example 5 and the catalyst of Example 15 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 60

The gaseous feed components are metered through mass flow controllers into the bottom of the reactor through the preheat leg. The catalyst is a mixture of the catalyst of Example 1 and the catalyst of Example 16 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 2.2 seconds. Results similar to Example 42 are obtained, selectivity and yield to acrylonitrile being several times that of the yield and selectivity to propylene.

EXAMPLE 61

The gaseous feed components are metered through mass flow controllers into the bottom of the reactor through the preheat leg. The catalyst is a mixture of the catalyst of Example 7 and the catalyst of Example 17 in the weight ratio of the former to the latter of 0.15. Water is introduced through a septum at the top of the preheat leg, using a syringe pump. The reaction temperature is 470° C. and the molar feed ratios are 5 propane/$1NH_3$/$2O_2$/$1H_2O$. The contact time is 3.0 seconds. Results similar to Example 42 are obtained, selectivity and yield to acrylonitrile being several times that of the yield and selectivity to propylene.

EXAMPLE 62

The gaseous feed components are metered through mass flow controllers into the bottom of the reactor through the preheat leg. The catalyst is a mixture of the catalyst of Example 6 and the catalyst of Example 18 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 63

The gaseous feed components are metered through mass flow controllers into the bottom of the reactor through the preheat leg. The catalyst is a mixture of the catalyst of Example 5 and the catalyst of Example 19 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 64

The gaseous feed components are metered through mass flow controllers into the bottom of the reactor through the preheat leg. The catalyst is a mixture of the catalyst of Example 5 and the catalyst of Example 20 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 65

The gaseous feed components ae metered through mass flow controllers into the bottom of the reactor through the preheat leg. The catalyst is a mixture of the catalyst of Example 4 and the catalyst of Example 21 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 66

The gaseous feed components are metered through mass flow controllers into the bottom of the reactor through the preheat leg. The catalyst is a mixture of the catalyst of Example 1 and the catalyst of Example 22 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 67

The gaseous feed components are metered through mass flow controllers into the bottom of the reactor through the preheat leg. The catalyst is a mixture of the catalyst of Example 5 and the catalyst of Example 23 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the yield and selectivity to propylene.

EXAMPLE 68

The gaseous feed components are metered through mass flow controllers into the bottom of the reactor through the preheat leg. The catalyst is a mixture of the catalyst of Example 1 and the catalyst of Example 24 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 1.2 seconds. Results similar to Example 42 are obtained, selectivity and yield to acrylonitrile being several times that of the selectivity and yield to propylene.

EXAMPLE 69

The gaseous feed components are metered through mass flow controllers into the bottom of the reactor through the preheat leg. The catalyst is a mixture of the catalyst of Example 5 and the catalyst of Example 25 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 1.2 seconds. Results similar to Example 42 are obtained, selectivity and yield to acrylonitrile being several times that of the selectivity and yield to propylene.

EXAMPLE 70

The gaseous feed components are metered through mass flow controllers into the bottom of the reactor through the preheat leg. The catalyst is a mixture of the catalyst of Example 4 and the catalyst of Example 26 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 1.2 seconds. Results similar to Example 42 are obtained, selectivity and yield to acrylonitrile being several times that of the selectivity and yield to propylene.

EXAMPLE 71

The gaseous feed components are metered through mass flow controllers into the bottom of the reactor through the preheat leg. The catalyst is a mixture of the catalyst of Example 7 and the catalyst of Example 27 in the weight ratio of the former to the latter of 0.15. Water is introduced through a septum at the top of the preheat leg, using a syringe pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the selectivity and yield to propylene.

EXAMPLE 72

The gaseous feed components are metered through mass flow controllers into the bottom of the reactor through the preheat leg. The catalyst is a mixture of the catalyst of Example 6 and the catalyst of Example 28 in the weight ratio of the former to the latter of 0.15. Water is introduced through a septum at the top of the preheat leg, using a syring pump. The reaction temperature is 470° C. and the molar feed ratios are 5 propane/1NH$_3$/2O$_2$/1H$_2$O. The contact time is 2.2 seconds. Results similar to Example 42 are obtained, selectivity and yield to acrylonitrile being several times that of the selectivity and yield to propylene.

EXAMPLE 73

The gaseous feed components were metered through mass flow controllers into the bottom of the reactor through the preheat leg. The catalyst was a mixture of the catalyst of Example 29 and the catalyst of Example 3 in the weight ratio of the former to the latter of 0.036. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.8 seconds. Analysis of the reactor effluent showed that propane conversion was 10.4 percent; yield and selectivity of propane to acrylonitrile were 6.0 and 57.6%, respectively; selectivity to propylene was 9.0%.

COMPARATIVE EXAMPLE I

The gaseous feed components were metered through mass flow controllers into the bottom of the reactor through the preheat leg. The catalyst was the catalyst of Example 29 alone. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of the reactor effluent showed that propane conversion was 20.7 percent; yield and selectivity of propane to acrylonitrile were 4.5% and 21.7%, respectively; selectivity to propylene was 48.0%.

EXAMPLE 74

The gaseous feed components were metered through mass flow controllers into the bottom of the reactor through the preheat leg. The catalyst was a mixture of the catalyst of Example 30 and the catalyst of Example 32 in the weight ratio of the former to the latter of 0.035. Water was introduced through a septum at the top of the preheat leg, using a syringe pump. The reaction temperature was 470° and the molar feed ratios were 5 propane/1NH$_3$/2O$_2$/1H$_2$O. The contact time was 2.1 seconds. Analysis of the reactor effluent showed that propane conversion was 11.2 percent; yield and selectivity of propane to acrylonitrile were 5.9% and 52.2%, respectively; selectivity to propylene was 9.8.

COMPARATIVE EXAMPLE J

The gaseous feed components were metered through mass flow controllers into the bottom of the reactor through the preheat leg. The catalyst was the catalyst of Example 30 alone. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of the reactor effluent showed that propane conversion was 20.4 percent; yield and selectivity of propane to acrylonitrile were 4.1 and 20.1, respectively; selectivity to propylene was 48.6.

COMPARATIVE EXAMPLE K

The gaseous feed components were metered through mass flow controllers into the bottom of the reactor through the preheat leg. The catalyst was a mixture of the catalyst of Example 31 and the catalyst of Example 32 in the weight ratio of the former to the latter of 0.035. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.0 seconds. Analysis of the reactor effluent showed that propane conversion was 9.9 percent; yield and selectivity of propane to acrylonitrile were 4.7 and 47.8%, respectively; selectivity to propylene was 8.9.

As will be evident to those skilled in the art various modifications of this invention can be made or followed in the light of the foregoing disclosure and discussion without departing from the spirit and scope of the disclosure or from the scope of the claims.

We claim:

1. A process for the ammoxidation of a paraffin selected from propane and isobutane to acrylonitrile or methacrylonitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:NH$_3$ in the range from 2 to 16 and a mole ratio of paraffin to O$_2$ in the range from 1 to 10, said first catalyst composition being 10–99 weight percent of a diluent/support and 90–1 weight percent of a catalyst having the components in the proportions indicated by the empirical formula:

$$VSb_mA_aG_bJ_cT_tO_x, \qquad \text{formula (1)}$$

where
A is one or more of W, Sn, Mo, B, P and Ge;
G is one or more of Fe, Co, Ni, Cr, Pb, Mn, Zn, Se, Te, Ga, In and As;
J is one or more of an alkali metal and Tl;
T is one or more of Ca, Sr and Ba; and where m is from 0.01 and up to 20; a is 0.2–10; b is 0–20; c is 0–1; t is 0–20; the ratio (a+b+c+t):(1+m) is 0.01–6; wherein x is determined by the oxidation state of other elements, and wherein the antimony has an average valency higher than +3 and the vanadium has an average valency lower than +5, said second catalyst composition being 0–99 weight percent of a diluent/support and 100–1 weight percent of a catalyst having the components in the proportions indicated by the empirical formula:

$$Bi_nCe_pD_dE_eL_fMo_{12}W_gO_y \qquad \text{formula (2)}$$

where
D is one or more of Fe, Mn, Pb, Co, Ni, Cu, Sn, P, Cr, Y, Mg, Ca, Sr, Ba and rare earths other than Ce and Sm;
E is one or more of Sb, Ge, As, Se, Te and V
L is one or more of an alkali metal, Tl, Ag and Sm and where n is 0.01–24, p is 0.01–24, (n+p) is 0.1–24, d is 0–10, e is 0–10, f is 0–6, g is 0–8, and y is determined by the oxidation state of the other elements, wherein the weight ratio in said mixture of said first catalyst composition to said second catalyst composition is in the range of 0.001 to 2.5.

2. A process of claim 1 wherein said mole ratio of paraffin:$NH_3$ is in the range from 3 to 7.

3. A process of claim 1 wherein said mole ratio of paraffin:$O_2$ is in the range from 1.5 to 5.

4. A process of claim 2 wherein said mole ratio of paraffin:$O_2$ is in the range from 1.5 to 5.

5. A process according to claim 1 wherein the mole ratio of $O_2$ to $NH_3$ in the feed to the reaction zone is in the range from 1 to 10.

6. A process according to claim 1 wherein the mole ratio of inert gaseous diluent to paraffin in the feed to the reaction zone is in the range from zero to 5.

7. A process of claim 1 wherein A includes at least 0.2 atoms of W per atom of v and the total A atoms include at least 0.4 (W atoms + Sn atoms) per atom of V.

8. A process of claim 1 wherein A includes at least 0.2 atoms of W per atom of V.

9. A process of claim 8 wherein A includes at least 0.4 atoms of P per atom of V.

10. A process of claim 1 wherein said support for the catalyst of formula (1) is selected from silica, alumina, titania, silica-niobia, silica-zirconia, silica-titania, silica-alumina, $Nb_2O_5$ and magnesia.

11. A process of claim 8 wherein said support for the catalyst of formula (1) is selected from silica-alumina and alumina having 20-100 weight percent alumina; silica-titania and titania having 20-100 weight percent titania; silica-zirconia and zirconia having 80-100 weight percent zirconia; and silica-niobia and niobia having 30-100 weight percent niobia ($Nb_2O_5$).

12. A process of any one of claims 1-9, wherein said diluent/support in said first catalyst composition comprises 20-100 weight percent alumina and 80 to zero weight percent silica.

13. A process of claim 12 wherein said diluent/support in said first catalyst composition comprises 50-100 weight percent alumina and 50 to zero weight percent silica.

* * * * *

UNITED STATES PATENT AND TRADEMARK OFFICE
CERTIFICATE OF CORRECTION

PATENT NO.   : 4,783,545
DATED        : November 8, 1988
INVENTOR(S)  : Linda C. Glaeser et al It is certified that error appears in the above-identified patent and that said Letters Patent is hereby corrected as shown below:

Column 31, line 18, "v" should read -- V --.

Signed and Sealed this

Ninth Day of May, 1989

Attest:

DONALD J. QUIGG

Attesting Officer

Commissioner of Patents and Trademarks